United States Patent [19] [11] 4,322,533
Lesher et al. [45] Mar. 30, 1982

[54] 1H-INDOLE-2,3-DIONE DERIVATIVES

[76] Inventors: George Y. Lesher, R.D. 1, Box 268; Donald F. Page, 21 Alva St.; Monte D. Gruett, Box 304A, Elliot Rd., all of East Greenbush, N.Y. 12061

[21] Appl. No.: 225,773

[22] Filed: Jan. 16, 1981

Related U.S. Application Data

[63] Continuation-in-part of Ser. No. 130,622, Mar. 17, 1980, abandoned.

[51] Int. Cl.$^3$ .................. C07D 401/04; C07D 401/06
[52] U.S. Cl. .................................... 546/273; 546/256; 424/263
[58] Field of Search ................................ 546/256, 273

[56] References Cited

PUBLICATIONS

Kost et al., Khim. Geterostsikl. Soedin., vol. 2, No. 5, (1966), pp. 722-728.
Sundberg, "The Chemistry of Indoles", 1970, p. 382, Academic press.
Karrer, "Organic Chemistry", Elsevier Pub. Co., N.Y. (1950), p. 253.
Fuson, "Advanced Organic Chemistry", John Wiley, N.Y. (1950), pp. 168, 370-371.
Chem. Abs. 66, 115538m (1967).
Hartman et al., Helv. Chim. Acta, 19, 1327-1332 (1936).
Bauer et al., Brit. J. Pharmacol., 15, 101-110 (1960).

*Primary Examiner*—Joseph Paul Brust
*Attorney, Agent, or Firm*—William G. Webb; B. Woodrow Wyatt

[57] ABSTRACT

1-$R_1$-4- or 5-[4-pyridinyl-($CH_2$)$_n$]-1H-indole-2,3-dione 3-Q derivatives, useful as cardiotonics, bronchodilators, anti-asthmatics, anti-allergics and anti-cholinergics, are prepared by cyclization of N-{3- or 4-[4-pyridinyl-($CH_2$)$_n$]phenyl}glyoxalamide oxime with acid; reaction of the product thus obtained with a carbonyl reactive reagent to prepare a compound where Q is other than O; and reaction of a compound where Q is either O or other than O with a lower-alkyl, hydroxy-lower-alkyl or di-lower-alkylamino-lower-alkyl ester of a strong mineral acid or with a carbo-lower-alkoxy-lower-alkyl halide to prepare compounds where $R_1$ is other than hydrogen.

48 Claims, No Drawings

1H-INDOLE-2,3-DIONE DERIVATIVES

RELATED APPLICATIONS

This is a continuation-in-part of our prior, copending application Ser. No. 130,622, filed Mar. 17, 1980, abandoned Jan. 16, 1981.

BACKGROUND OF THE INVENTION (a) Field of the Invention

This invention relates to 4- and 5-[4-pyridinyl-$(CH_2)_n$]-1H-indole-2,3-dione derivatives useful as cardiotonics, bronchodilators and anti-asthmatics.

(b) The Prior Art

Kost et al., Khim. Geterostsikl. Soedin., 5, 722–728 (1966); Chem. Abs. 66, 115538m (1967) disclose 1-lower-alkyl-5-(4-pyridinyl)-1,2-dihydroindoles for which no utility is disclosed.

Hartman et al., Helv. Chim. Acta, 19, 1327–1332 (1936) disclose 1H-indole-2,3-dione derivatives substituted in the 5-position by an amino, acetylamino or dimethylamino group. No utility for the compounds is disclosed.

Bauer et al., Brit. J. Pharmacol., 15, 101–110 (1960) disclose 1-lower-alkyl-1H-indole-2,3-dione 3-thiosemicarbazones useful as anti-viral agents.

5-Methyl-1H-indole-2,3-dione is a known, commercially available compound which finds use as an intermediate for organic synthesis.

SUMMARY OF THE INVENTION

In a composition of matter aspect, this invention relates to certain 1-$R_1$-4- or 5-[4-pyridinyl-$(CH_2)_n$]-1H-indole-2,3-dione 3-Q derivatives and their acid-addition salts, useful as cardiotonics, bronchodilators, anti-asthmatics, anti-allergics and anti-cholinergics.

In a process aspect, this invention relates to a process for preparing the 1-$R_1$-4- or 5-[4-pyridinyl-$(CH_2)_n$]-1H-indole-2,3-dione 3-Q derivatives of the invention which comprises cyclizing an N-{3- or 4-[4-pyridinyl-$(CH_2)_n$]phenyl}-glyoxalamide oxime in the presence of a strong mineral acid in order to prepare a 4- or 5-[4-pyridinyl-$(CH_2)_n$]-1H-indole-2,3-dione; if desired, reacting the latter with a carbonyl reactive reagent in order to prepare a 4- or 5-[4-pyridinyl-$(CH_2)_n$]-1H-indole-2,3-dione 3-Q derivative; and, if desired, reacting the 4- or 5-[4-pyridinyl-$(CH_2)_n$]-1H-indole-2,3-dione where Q is either O or the moiety resulting from the carbonyl reactive reagent with a lower-alkyl, hydroxy-lower-alkyl or di-lower-alkylamino-lower-alkyl ester of a strong mineral acid or with a carbo-lower-alkoxy-lower-alkyl halide in the presence of an acid-acceptor to prepare a 1-lower-alkyl-4- or 5-[4-pyridinyl-$(CH_2)_n$]-1H-indole-2,3-dione 3-Q derivative, where Q is either O or other than O as defined below, and $R_1$ is other than hydrogen as defined below.

DETAILED DESCRIPTION INCLUSIVE OF THE PREFERRED EMBODIMENTS

More specifically, this invention provides valuable compounds having the formula:

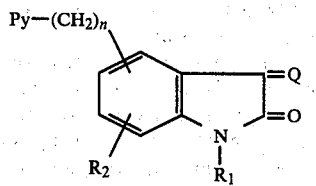

I where Py represents the 4-pyridinyl group; $R_1$ represents hydrogen, lower-alkyl, hydroxy-lower-alkyl (having from two to seven carbon atoms, at least two of which are linear), di-lower-alkylamino-lower-alkyl or carbo-lower-alkoxy-lower-alkyl; $R_2$ represents hydrogen or lower-alkyl; Q represents O, H(OH), NOH, $NNH_2$, NNH(lower-alkyl), NN(lower-alkyl)$_2$, $NNHC_6H_5$, NNH(hydroxy-lower-alkyl) (having from two to seven carbon atoms, at least two of which are linear), NNHC(=S)$NH_2$, NNHC(=NH)$NH_2$ (only when $R_1$ is lower-alkyl), $NNHCOCH_2N$(lower-alkyl)$_3^+X^-$ or $NNHCOCH_2$-Pyr$^+X^-$, where Pyr$^+$ is the pyridinium cation and $X^-$ in the latter two instances is the anion of a strong mineral acid; n is 0 (zero) or the integer 1; the 4-pyridinyl-$(CH_2)_n$ group occupies either the 4- or 5-position of the 1H-indole-2,3-dione nucleus; and the N-(Py)-oxides thereof, which are useful as cardiotonics, bronchodilators, anti-asthmatics, anti-allergics and anti-cholinergics.

The compounds of formula I above are thus either 1H-indole-2,3-diones (Q is O); the reduced 2-oxo-1H-indol-3-ol derivatives thereof [Q is H(OH)]; or the 3-oximes (Q is NOH), 3-hydrazones (Q is $NNH_2$), 3-lower-alkylhydrazones [Q is NNH(lower-alkyl)], 3-di-lower-alkylhydrazones [Q is NN (lower-alkyl)$_2$], 3-phenyl-hydrazones [Q is $NNHC_6H_5$], 3-(hydroxy-lower-alkyl)-hydrazones [Q is NNH(hydroxy-lower-alkyl)], 3-thiosemicarbazones [Q is NNHC(=S)$NH_2$], 3-imidosemicarbazones [Q is NNHC(=NH)$NH_2$], 3-[(tris-lower-alkyl quarternary ammonium)-acetyl]hydrazones [Q is $NNHCOCH_2$—N(lower-alkyl)$_3^+X^-$] or 3-(pyridinium acetyl)hydrazones [Q is $NNHCOCH_2$—Pyr$^+X^-$] thereof.

The above-indicated limitation in the definition of the group Q as NNHC(=NH)$NH_2$ is made in order to exclude from the ambit of the invention species which have been found to be inactive as cardiotonics, bronchodilators, anti-asthmatics, anti-allergics or anti-cholinergics. However the species where Q is NNHC(=NH)$NH_2$ and $R_1$ is hydrogen are useful as intermediates for preparing the corresponding species where $R_1$ is lower-alkyl, which latter species are useful for the purposes of the present invention. The compounds where Q is NNHC(=NH)$NH_2$ and $R_1$ is hydrogen are thus considered to be within the purview of the present invention.

The compounds within the ambit of formula I which have been found useful as cardiotonics are those where each of $R_1$, Q and n has each of the meanings given above, except for the species where Q is NN(lower-alkyl)$_2$ or $NNHC_6H_5$, the species where $R_1$ is di-lower-alkylamino-lower-alkyl or carbo-lower-alkoxy-lower-alkyl and the N-(Py)-oxides of the subject compounds.

The compounds within the ambit of formula I which have been found useful as bronchodilators, anti-asthmatics, anti-allergics and anti-cholinergics are those where each of $R_1$, Q and n has each of the meanings given above, except for the species where Q is NOH, NNHC(=NH)NH$_2$, NNHCOCH$_2$N(lower-alkyl)$_3$+X− or NNHCOCH$_2$—Pyr+X− and the species where R$_1$ is hydroxy-lower-alkyl.

Except as defined above in connection with the NNH(hydroxy-lower-alkyl) moiety as one of the definitions of the group Q and the hydroxy-lower-alkyl moiety as one of the definitions of the group R$_1$, the term lower-alkyl as used herein otherwise means a saturated, acyclic group which may be straight or branched and containing from one to about seven carbon atoms as exemplified by methyl, ethyl, propyl, isopropyl, n-butyl, t-butyl, pentyl, hexyl or heptyl.

The anion represented by X− in the compounds of formula I where Q is NNHCOCH$_2$N(lower-alkyl)$_3$+X− or NNHCOCH$_2$—Pyr+X− is the anion of a strong mineral acid such as a hydrohalic acid (i.e. hydrofluoric acid, hydrochloric acid, hydrobromic acid or hydriodic acid), sulfuric acid or the like.

The compounds of formula I are prepared using a modification of the Sandmeyer isonitrosoacetanilide isatin synthesis, described in detail in Organic Syntheses, Coll. Vol. I, 327 (1941), which involves reaction of an appropriate 3- or 4-[4-pyridinyl-(CH$_2$)$_n$]aniline of formula II with chloral hydrate and hyroxylamine in an acid medium and cyclization of the resulting N-{3- or 4-[4-pyridinyl-(CH$_2$)$_n$]phenyl}glyoxalamide oxime of formula III with concentrated sulfuric acid to produce the compounds of formula I where R$_1$ is hydrogen and Q is O. The initial reaction to prepare the glyoxalamide oximes of formula III is carried out by adding an aqueous solution of chloral hydrate and sodium sulfate to an aqueous solution of the 3- or 4-[4-pyridinyl-(CH$_2$)$_n$]aniline of formula II containing a molar excess of a mineral acid at ambient temperature and, after formation of the glyoxalamide, treating the aqueous solution with an aqueous solution of hydroxylamine in the form of an acid-addition salt thereof and, if desired, warming the mixture to effect complete solution of all reactants and the product. Cyclization of the glyoxalamide oximes of formula III to the compounds of formula I is carried out by heating a solution of the former in concentrated sulfuric acid at a temperature in the range from around 30° to 100° C.

The compounds of formula I where R$_1$ is hydrogen and Q is O thus prepared can then be subsequently reacted with an appropriate carbonyl reactive reagent, for example hydroxylamine, hydrazine, a lower-alkyl-hydrazine, a di-lower-alkylhydrazine, phenylhydrazine, a hydroxy-lower-alkylhydrazine, thiosemicarbazide, imidosemicarbazide, a tris-lower-alkyl quaternary ammonium acethydrazide salt or a pyridinium-acethydrazide salt to give the compounds of formula I where Q is, respectively, NOH, NNH$_2$, NNH(lower-alkyl), NN(lower-alkyl)$_2$, NNHC$_6$H$_5$, NNH(hydroxy-lower-alkyl), NNHC(=S)NH$_2$, NNHC(=NH)NH$_2$, NNHCOCH$_2$N(lower-alkyl)$_3$+X− or NNHCOCH$_2$—Pyr+X−; and R$_1$ is hydrogen.

The reaction of the compounds of formula I where R$_1$ is hydrogen and Q is O with a carbonyl reactive reagent is carried out by heating a mixture of the starting material of formula I with the appropriate carbonyl reactive compound in an inert organic solvent. Suitable solvents are lower-alkanols (for example methanol, ethanol, isopropanol or the like) or a lower-alkanoic acid (for example acetic acid). The use of an acid catalyst, for example acetic acid or hydrochloric acid, is advantageous. The reaction takes place at a temperature in the range from 20° to 90° C.

The compounds of formula I thus prepared are then reacted with a lower-alkyl, hydroxy-lower-alkyl or di-lower-alkylamino-lower-alkyl ester of a strong mineral acid, for example a hydrohalic acid or sulfuric acid, or with a carbo-lower-alkoxy-lower-alkyl halide, in the presence of an acid-acceptor, to produce the compounds of formula I where R$_1$ is, respectively, lower-alkyl, hydroxy-lower-alkyl, di-lower-alkylamino-lower-alkyl or carbo-lower-alkoxy-lower-alkyl, and Q is other than O. Alternatively the compounds of formula I where Q is O and R$_1$ is hydrogen can be alkylated to produce the compounds where R$_1$ is lower-alkyl, hydroxy-lower-alkyl, di-lower-alkylamino-lower-alkyl or carbo-lower-alkoxy-lower-alkyl and Q is O.

Alkylation of the compounds of formula I where R$_1$ is hydrogen is carried out by reaction of the latter with an appropriate lower-alkyl, hydroxy-lower-alkyl or di-lower-alkylamino-lower-alkyl ester of a strong mineral acid, for example a halide or sulfate, or with a carbo-lower-alkoxy-lower-alkyl halide, in an inert organic solvent, for example a lower-alkanol, acetone or dimethylformamide (DMF), in the presence of a molar equivalent amount of an acid-acceptor, for example an alkali metal hydride or alkali metal carbonate. The reaction is carried out at a temperature in the range from 20° to about 90° C.

The overall synthetic method is illustrated by the reaction sequence:

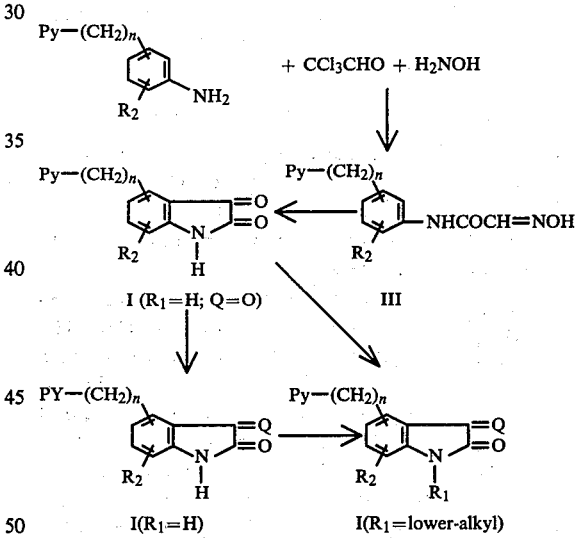

where R$_1$, R$_2$, Q, Py and n have the meanings given above.

The compounds where Q is H(OH) are prepared by reduction of the corresponding compounds where Q is O with sodium hydrosulfite. The reaction is carried out by heating the reactants in an aqueous medium at the reflux temperature thereof.

The N-(Py)-oxides of the compounds of formula I are prepared by oxidizing the latter with an organic peracid, for example performic, peracetic, perbenzoic or 3-chloroperbenzoic acids. The reaction is preferably carried out in an inert organic solvent, for example a lower-alkanoic acid, and at a temperature in the range from 15°–60° C.

The compounds of formula II where n is 0 are generally known, having been described by Heilbron et al., J. Chem. Soc., 1279(1940); Forsyth et al., J. Chem. Soc., 2921(1926); and British Pat. No. 518,886. The compounds where n is 1 are prepared from the commercially available Py(CH$_2$)$_n$-substituted nitrobenzenes by reduction of the latter with hydrogen over a platinum oxide catalyst in acetic acid at a hydrogen pressure around 55 p.s.i.g.

Due to the presence of a basic amino grouping in the 4-pyridinyl (Py) moiety, the free base form represented by formula I above reacts with organic and inorganic acids to form acid-addition salts. The acid-addition salt forms are prepared from any organic or inorganic acid. They are obtained in conventional fashion, for instance either by direct mixing of the base with acid or, when this is not appropriate, by dissolving either or both the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid and the like.

All of the acid-addition salts are useful as sources of the free base forms which are generated by reaction of the salts with an inorganic base. It will thus be appreciated that if one or more of the characteristics, such as solubility, molecular weight, physical appearance, toxicity, or the like of a given base or acid-addition salt thereof render that form unsuitable for the purpose at hand, it can be readily converted to another, more suitable form. For pharmaceutical purposes, acid-addition salts of relatively non-toxic pharmaceutically-acceptable acids, for example hydrochloric acid, lactic acid, tartaric acid, methanesulfonic acid and the like are of course employed.

With the exceptions previously noted in the definitions of Q and R$_1$, the compounds of formula I, and their acid-addition salts, have been found to be useful as cardiotonics. Their utility as cardiotonics was established by their effectiveness in standard pharmacological test procedures, for example in causing a significant increase in the contractile force of the isolated cat atria and papillary muscle, that is greater than 25% increase in papillary muscle force and right atrial force, while causing only a lower percentage increase (about one-third or less than the percentage increase in right atrial or papillary muscle force) in right atrial rate and also in causing a significant increase in the cardiac contractile force in the anesthetized dog with low or minimal changes in heart rate and blood pressure, that is, an increase of greater than 25% in cardiac contractile force (or cardiac contractility) and less than 25% change in heart rate and blood pressure. The isolated cat atria and papillary muscle procedure and the anesthetized dog procedure are described in detail by Alousi et al., Circ. Research, 45 666–667 (1979).

With the other exceptions previously noted in the definitions of Q and R$_1$, the compounds of formula I, and their acid-addition salts, have been found to be useful as bronchodilators, anti-asthmatics, anti-allergics and anti-cholinergics.

Their utility as bronchodilators, anti-asthmatics, anti-allergics and anti-cholinergics was established by their effectiveness in standard pharmacological test procedures, for example the passive cutaneous anaphylaxis test in rats described by Mielens et al., Int. Arch. Allergy, 47, 633–649 (1974); a modified procedure of the bronchoconstriction activity test in dogs described by Minatoya, J. Pharm. Exp. Therap., 206, 515–527 (1978); the anaphylactic bronchoconstriction activity test in guinea pigs, a modified procedure of Miller et al., Brit. J. Pharmacol., 58, 442P–443P (1976); and a modification of the human basophils test described by Margo Immunochem., 12, 389 (1975) and by Conroy et al. Monogr. Allergy, 14, 307–309 (1979).

Bronchoconstrictor activity was also determined using a test procedure based on bronchoconstriction induced by histamine, acetylcholine and immune complex in guinea pigs which procedure is described as follows: guinea pigs of either sex, weighing 250–350 g. each, was fasted overnight, then anesthetized with 1.5 g. of urethane/kg. (i.p.), and the jugular vein and trachea were cannulated. The guinea pigs thus prepared were artificially respired with a rodent pump, and the intratracheal pressure was recorded continuously using a Statham transducer on a Grass polygraph. At five minute intervals, 5 $\mu$g./kg. of histamine phosphate (determined as base) was injected intravenously in order to ascertain that the maximum achievable bronchoconstrictor responsiveness (i.e. the increase in intratracheal pressure in mm.Hg) had been obtained, and the average of the last two increases in the intratracheal pressure was recorded. Acetylcholine was then injected intravenously at 15 $\mu$g./kg. five minutes after the last injection of histamine, and the increase in intratracheal pressure was again recorded. Two minutes following the injection of acetylcholine, 0.1 mg./kg. of propranolol was injected intravenously, and immune complexes [pure antibovine serum albumin (BSA) antibody/BSA complexes dissolved in excess BSA] were injected intravenously at 1.0 mg./kg. (in terms of their antibody content) three minutes following the injection of propranolol, and the increase in intratracheal pressure was again recorded.

Inhibition of bronchoconstriction was scored for each of the bronchoconstriction-inducers (i.e. histamine, acetylcholine and immune complex) with respect to the average bronchoconstriction in negative control guinea pigs (minimum of four guinea pigs in four days) according to the following criteria:

| % Inhibition | Score |
| --- | --- |
| 81–100 | 4 |
| 61–80 | 3 |
| 41–60 | 2 |

| % Inhibition | Score |
|---|---|
| 21-40 | 1 |
| 0-20 | 0 |

Test compounds scoring 3 or 4 against the three broncho-constriction-inducers were considered active; those scoring 2 were considered marginally active; and those scoring 0 or 1 were considered inactive. Aminophylline, which was used as a reference drug, gave scores from 3-3-2 to 4-4-3 for bronchoconstriction induced by histamine, acetylcholine and immune complex, respectively.

Generally speaking, the various bronchoconstrictor activity tests described above, i.e. the histamine induced bronchoconstriction activity test in dogs (Minatoya) and the histamine/acetylcholine/immune complex-induced bronchoconstriction test in guinea pigs, are used to define bronchodilator activity, while the passive cutaneous anaphylaxis test and the human basophils test can be used to define anti-allergic activity. Moreover, activity by test species against one of the types of bronchoconstriction in guinea pigs (induced by histamine, acetylcholine or immune complex) can indicate utility, respectively, as anti-histamines, anti-cholinergics or prostaglandin synthetase inhibitors. Species useful as anti-asthmatics ideally show both bronchodilator and anti-allergic parameters of activity, but species useful for such purpose can have either parameter alone without the other.

The actual determination of the numerical pharmacological data for a particular compound of the invention is readily obtained according to the above-described standard test procedures by technicians versed in pharmacological test procedures without the need for any extensive experimentation.

In clinical practice, the compounds of formula I are normally administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, for example lubricating agents such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents, such compositions can also contain adjuvants, such as wetting and suspending agents, sweetening, flavoring, perfuming and preserving agents. According to this invention, the compounds for oral administration also include capsules of adsorbable material such as gelatin containing the active component either with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. The compositions can also contain adjuvants such as stabilizing, preserving, wetting, emulsifying and dispersing agents.

They can be sterilized, for example by filtration through a bacteria-retaining filter, by incorporation of sterilizing agents in the compositions, by irradiation or by heating. They can also be manufactured in the form of sterile solid compositions, which can be dissolved in sterile water or some other sterile injectable medium immediately before use.

The percentages of active component in such compositions may be varied so that a suitable dosage is obtained. The dosage administered to a particular patient is variable, depending upon the clinician's judgment using as criteria: the route of administration, the duration of treatment, the size and physical condition of the patient, the potency of the active component and the patient's response thereto. An effective dosage amount of the active component can thus only be determined by the clinician after a consideration of all criteria and utilizing his best judgment on the patient's behalf.

The structures of the compounds of the invention were established by the mode of synthesis, by elementary analyses and by ultraviolet, infrared and nuclear magnetic resonance spectra. The course of reactions were followed, and the homogeneity of the products were ascertained, by thin layer chromatography.

The manner and process of making and using the invention, and the best mode contemplated by the inventors of carrying out the invention, will now be described so as to enable any person skilled in the art to which it pertains to make and use the same. The melting points are uncorrected.

EXAMPLE 1A

To a solution of 9.0 g. (0.054 mole) of chloral hydrate, 57 g. of sodium sulfate and 8.5 g. (0.05 mole) of 3-(4-pyridinyl)benzenamine in 225 ml. of water containing 4.3 ml. of concentrated hydrochloric acid was added a solution of 11.0 g. (0.16 mole) of hydroxylamine hydrochloride, and the mixture was stirred with warming for thirty minutes and then heated to boiling for five minutes. The mixture was then allowed to cool to ambient temperature, and the solid which separated was collected to give 12.8 g. of crude product which was recrystallized from water to give 9.7 g. of N-[3-(4-pyridinyl)phenyl]glyoxalamide oxime hydrochloride, m.p. 207°-208° C.

The latter (100 g., of 0.36 mole) was added with stirring to 350 ml. of sulfuric acid at 60° C. over a thirteen minute period while maintaining the temperature around 85°-90° C. by cooling, as necessary, with an ice bath. The dark solution was then poured onto about 3 kg. of crushed ice, and when the ice had melted the mixture was neutralized by the careful addition of solid sodium carbonate until the mixture was alkaline (pH 9-10), water being added as necessary to facilitate stirring. The mixture was filtered, and the solid material was washed repeatedly with boiling water and recrystallized from DMF to give 26.4 g. of 4-(4-pyridinyl)-1H-indole-2,3-dione, m.p. >300° C.

A small amount of the free base was suspended in water, the suspension was treated with concentrated hydrochloric acid until the solid dissolved, and the solvent was removed in vacuo to give 4-(4-pyridinyl)-1H-indole-2,3-dione hydrochloride, m.p. >300° C.

Following a procedure similar to that described in Example 1A above, the following compounds of formula I where $R_1$ is hydrogen and Q is O were prepared.

EXAMPLE 1B 5-(4-Pyridinyl)-1H-indole-2,3-dione, m.p. 305°–308° C. (14.3 g. from DMF), prepared by reaction of 85.1 g. (0.05 mole) of 4-(4-pyridinyl)benzenamine with 110 g. (0.66 mole) of chloral hydrate and 110 g. (1.58 moles) of hydroxylamine hydrochloride in a total of 2850 ml. of water in the presence of 570 g. (4.0 moles) of sodium sulfate and 46 ml. of concentrated hydrochloric acid and cyclization of 37.6 g. (0.14 mole) of the resulting N-[4-(4-pyridinyl)phenyl]glyoxalamide oxime hydrochloride (108.6 g., m.p. 215°–220° C. from isopropanol) in 200 ml. of concentrated sulfuric acid. A sample recrystallized from water gave material having m.p. 231°–232° C.

A sample of the free base was converted to the methanesulfonate salt to give 5-(4-pyridinyl)-1H-indole-2,3-dione methanesulfonate, m.p. 235°–237° C. (from DMF/diethyl ether).

EXAMPLE 1C 5-(4-Pyridinylmethyl)-1H-indole-2,3-dione, m.p. 247°–250° C. (16.1 g. from DMF), prepared by reaction of 17.79 g. (0.097 mole) of 4-(4-pyridinylmethyl)benzenamine with 17.57 g. (0.11 mole) of chloral hydrate and 21.3 g. (0.31 mole) of hydroxylamine hydrochloride in a total of 528 ml. of water in the presence of 110.7 g. (0.78 mole) of sodium sulfate and 8.9 ml. of concentrated hydrochloric acid, and cyclization of the resulting (27.4 g., 0.09 mole) N-[4-(4-pyridinylmethyl)phenyl]glyoxalamide oxime hydrochloride with 100 ml. of concentrated sulfuric acid.

EXAMPLE 1D

4-Methyl-5-(4-pyridinyl)-1H-indole-2,3-dione, m.p. >315° C. (26.5 g., from DMF), prepared by reaction of 66 g. (0.36 mole) of 3-methyl-4-(4-pyridinyl)-benzenamine with 64.8 g. (0.39 mole) of chloral hydrate and 79.2 g. (1.19 mole) of hydroxylamine hydrochloride in a total of 1260 ml. of water in the presence of 410 g. (2.9 moles) of sodium sulfate and 34 ml. of concentrated hydrochloric acid, and cyclization of 64 g. (0.24 mole) of the resulting (82.5 g.) N-[3-methyl-4-(4-pyridinyl)-phenyl]glyoxalamide oxime hydrochloride with 180 ml. of concentrated sulfuric acid.

EXAMPLE 1E

6-Methyl-5-(4-pyridinyl)-1H-indole-2,3-dione, m.p. 292°–294° C. (6.7 g., from methanol), isolated as a second product from the mother liquors resulting from recrystallization of the 4-methyl-5-(4-pyridinyl)-1H-indole-2,3-dione described above in Example 1D.

EXAMPLE 2A

To a stirred suspension of 12.2 g. (0.05 mole) of 4-(4-pyridinyl)-1H-indole-2,3-dione in a solution of 300 ml. of ethanol and 13.5 ml. of acetic acid was added 8.1 g. (0.16 mole) of hydrazine hydrate, and the mixture was stirred and refluxed for twenty hours, then cooled and the solid collected by filtration. Recrystallization of the solid from DMF afforded 8.5 g. of 4-(4-pyridinyl)-1H-indole-2,3-dione 3-hydrazone, m.p. 253°–254° C.

Following a procedure similar to that described in Example 2A above, the following compounds of formula I, where $R_1$ is hydrogen and Q is other than O, were prepared:

EXAMPLE 2B 5-(4-Pyridinyl)-1H-indole-2,3-dione 3-hydrazone, m.p. 185°–187° C. (10.05 g., from DMF), prepared by refluxing a suspension of 13.45 g. (0.06 mole) of 5-(4-pyridinyl)-1H-indole-2,3-dione with 10.3 ml. of an 85% aqueous solution of hydrazine in 300 ml. of ethanol and 15 ml. of acetic acid.

A sample of the free base was reacted with concentrated hydrochloric acid in DMF/water to give 5-(4-pyridinyl)-1H-indole-2,3-dione 3-hydrazone hydrochloride, m.p. 285° C.

EXAMPLE 2C 5-(4-Pyridinylmethyl)-1H-indole-2,3-dione 3-hydrazone, m.p. 200°–202° C. (4.0 g., from aqueous DMF), prepared by refluxing a mixture of 5.48 g. (0.023 mole) of 5-(4-pyridinylmethyl)-1H-indole-2,3-dione with 3.95 ml. of 85% aqueous hydrazine in a solution of 115 ml. of ethanol and 25 ml. of acetic acid.

EXAMPLE 2D 5-(4-Pyridinyl)-1H-indole-2,3-dione 3-oxime hydrochloride hemihydrate, m.p. 275°–278° C. (6.84 g., from methanol/diethyl ether), prepared by refluxing a mixture of 11.21 g. (0.05 mole) of 5-(4-pyridinyl)-1H-indole-2,3-dione with 17.37 g. (0.25 mole) of hydroxylamine hydrochloride in 300 ml. of pyridine.

EXAMPLE 2E 5-(4-Pyridinyl)-1H-indole-2,3-dione 3-methylhydrazone, m.p. 244°–245° C. (7.2 g., from DMF containing 10% by volume of triethylamine), prepared by refluxing a mixture of 11.2 g. (0.05 mole) of 5-(4-pyridinyl)-1H-indole-2,3-dione with 3.5 g. (0.075 mole) of methylhydrazine in a solution of 300 ml. of ethanol and 10 ml. of acetic acid.

EXAMPLE 2F 5-(4-Pyridinyl)-1H-indole-2,3-dione 3-(t-butyl)hydrazone, m.p. 198°–199° C. (8.0 g., from ethanol), prepared by refluxing a mixture of 11.2 g. (0.05 mole) of 5-(4-pyridinyl)-1H-indole-2,3-dione with 9.4 g. (0.075 mole) of t-butylhydrazine hydrochloride in 300 ml. of ethanol.

EXAMPLE 2G 4-(4-Pyridinyl)-1H-indole-2,3-dione 3-(N,N-dimethyl)hydrazone, m.p. 213°–214° C. (4.5 g., from ethanol), prepared by refluxing a mixture of 6.6 g. (0.03 mole) of 4-(4-pyridinyl)-1H-indole-2,3-dione with 30 ml. of N,N-dimethylhydrazine in a solution of 150 ml. of ethanol containing fifteen drops of acetic acid.

EXAMPLE 2H 5-(4-Pyridinyl)-1H-indole-2,3-dione 3-dimethylhydrazone, m.p. 211°–212° C. (5.8 g., from isopropanol), prepared by refluxing a mixture of 11.2 g. (0.05 mole) of 5-(4-pyridinyl)-1H-indole-2,3-dione with 38.0 ml. (0.5 mole) of N,N-dimethylhydrazine in a solution of 300 ml. of ethanol and 10 ml. of acetic acid.

EXAMPLE 2J 5-(4-Pyridinyl)-1H-indole-2,3-dione 3-(2-hydroxyethyl)hydrazone, m.p. 244°–245° C. (11.0 g., from DMF containing about 5% by volume of triethylamine), prepared by reacting 11.2 g. (0.05 mole) of 5-(4-pyridinyl)-1H-indole-2,3-dione with 5.7 g. (0.075 mole) of (2- hydroxyethyl)hydrazine in a solution of 300 ml. of ethanol and 10 ml. of acetic acid.

EXAMPLE 2K 5-(4-Pyridinyl)-1H-indole-2,3-dione 3-thiosemicarbazone, m.p. >300° C. (9.9 g., from DMF), prepared by refluxing a mixture of 11.2 g. (0.05 mole) of 5-(4-pyridinyl)-1H-indole-2,3-dione with 6.8 g. (0.075 mole) of thiosemicarbazide and 1.5 g. of sodium acetate in 300 ml. of ethanol.

EXAMPLE 2L 5-(4-Pyridinyl)-1H-indole-2,3-dione imidosemicarbazone, m.p. >310° C. (23.8 g.), prepared by refluxing a mixture of 5-(4-pyridinyl)-1H-indole-2,3-dione and 20.4 g. (0.15 mole) of aminoguanidine bicarbonate in a solution of 600 ml. of absolute ethanol containing twenty drops of acetic acid.

EXAMPLE 2M 5-(4-Pyridinyl)-1H-indole-2,3-dione 3-[(trimethylammonium)acetyl]hydrazone chloride hemihydrate, m.p. >305° C. (6.64 g., from methanol/acetone), prepared by refluxing a mixture of 12.33 g. (0.055 mole) of 5-(4-pyridinyl)-1H-indole-2,3-dione and 9.7 g. (0.056 mole) of trimethylammonium acethydrazide chloride (Girard's reagent T) in 100 ml. of acetic acid.

EXAMPLE 2N 5-(4-Pyridinyl)-1H-indole-2,3-dione 3-phenylhydrazone, m.p. 280°–281° C. (9.5 g., from DMF), prepared by refluxing a mixture of 11.2 g. (0.05 mole) of 5-(4-pyridinyl)-1H-indole-2,3-dione and 8.1 g. (0.075 mole) of phenylhydrazine in a solution of 300 ml. of ethanol and 10 ml. of glacial acetic acid.

EXAMPLE 2P

4-Methyl-5-(4-pyridinyl)-1H-indole-2,3-dione 3-hydrazone, m.p. 238°–240° C. (11.7 g., from DMF), prepared by refluxing a mixture of 14 g. (0.06 mole) of 4-methyl-5-(4-pyridinyl)-1H-indole-2,3-dione and 8.8 g. (0.18 mole) of hydrazine hydrate in a solution of 15 ml. of ethanol and 15 ml. of acetic acid.

EXAMPLE 2Q

4-Methyl-5-(4-pyridinyl)-1H-indole-2,3-dione 3-[(trimethylammonium)acetyl]hydrazone chloride hemihydrate, m.p. 266°–268° C. (4.9 g., from ethanol), prepared by refluxing a mixture of 10 g. (0.042 mole) of 4-methyl-5-(4-pyridinyl)-1H-indole-2,3-dione and 8 g. (0.053 mole) of trimethylammonium acethydrazide chloride (Girard's Reagent T) in 200 ml. of ethanol and 10 ml. of glacial acetic acid.

EXAMPLE 2R 5-(4-Pyridinyl)-1H-indole-2,3-dione 3-(pyridiniumacetyl)hydrazone chloride dihydrochloride hydrate (4:3), m.p. >315° C. (16.34 g., from methanol), prepared by refluxing a mixture of 28.83 g. (0.09 mole) of 5-(4-pyridinyl)-1H-indole-2,3-dione and 17.22 g. (0.092 mole) of pyridinium acethydrazide chloride (Girard's Reagent P) in 200 ml. of glacial acetic acid in the presence of 7.38 g. (0.090 mole) of anhydrous sodium acetate.

EXAMPLE 3A

To a stirred suspension of 11.2 g. (0.05 mole) of 4-(4-pyridinyl)-1H-indole-2,3-dione and 7.6 g. (0.055 mole) of potassium carbonate in 75 ml. of DMF was added 7.8 g. (0.05 mole) of methyl iodide, and the mixture was stirred and heated gently on a steam bath for forty-five minutes. The mixture was then taken to dryness, the solid residue was partitioned between water and methylene dichloride, the organic layer was separated, and the aqueous layer was extracted with additional portions of methylene dichloride. The combined organic extracts, on evaporation to dryness, afforded 3.6 g. of an orange solid which was recrystallized from DMF to give 3.0 g. of 1-methyl-4-(4-pyridinyl)-1H-indole-2,3-dione, m.p. 231°–232° C.

Following a procedure similar to that described in Example 3A above, the following compounds of formula I, where $R_1$ is methyl, were prepared:

EXAMPLE 3B

1-Methyl-5-(4-pyridinyl)-1H-indole-2,3-dione, m.p. 198°–204° C. (2.12 g. from isopropanol), prepared by reaction of 0.48 g. (0.01 mole) of sodium hydride (as a 50% dispersion in mineral oil) with 2.24 g. (0.01 mole) of 5-(4-pyridinyl)-1H-indole-2,3-dione in 150 ml. of DMF and reaction of the resulting sodium salt with 0.69 ml. (0.01 mole) of methyl iodide.

EXAMPLE 3C

Ethyl α-[5-(4-pyridinyl)-1H-indole-2,3-dion-1-yl]-acetate methanesulfonate, m.p. 205°–207° C. (10.3 g., from ethanol), prepared by reaction of 2.7 g. (0.059 mole) of a 50% dispersion of sodium hydride in mineral oil with 11.2 g. (0.05 mole) of 5-(4-pyridinyl)-1H-indole-2,3-dione in 75 ml. of DMF, reaction of the resulting sodium salt with 5.6 ml. (0.05 mole) of ethyl bromoacetate and conversion of the final product to the methanesulfonate salt.

EXAMPLE 3D

1-[2-(Diethylamino)ethyl]-5-(4-pyridinyl)-1H-indole-2,3-dione trihydrochloride, m.p. 261°–265° C. (13.2 g., from ethanol), prepared by reaction of 7.2 g. (0.15 mole) of a 50% dispersion of sodium hydride in mineral oil with 33.6 g. (0.15 mole) of 5-(4-pyridinyl)-1H-indole-2,3-dione in 400 ml. of DMF, reaction of the resulting sodium salt with 20.2 g. (0.15 mole) of diethylaminoethyl chloride and conversion of the final product to the trihydrochloride salt.

EXAMPLE 3E t-Butyl α-[5-(4-pyridinyl)-1H-indole-2,3-dion-1-yl]acetate, m.p. 158°–160° C. (23.4 g., chromatographed on 800 g. of silica gel with 10% methanol in diethyl ether as eluent), prepared by reaction of 12 g. of (0.26 mole) of a 50% dispersion of sodium hydride in mineral oil with 57 g. (0.25 mole) of 5-(4-pyridinyl)-1H-indole-2,3-dione in 400 ml. of DMF and reaction of the resulting sodium salt with 50 g. (0.25 mole) of t-butyl bromoacetate.

EXAMPLE 3F 1-(2-Hydroxyethyl)-5-(4-pyridinyl)-1H-indole-2,3-dione, m.p. 214°–215° C. (4.7 g., from ethanol), prepared by reaction of 5.6 g. (0.12 mole) of a 50% dispersion of sodium hydride in mineral oil with 22.4 g. (0.1 mole) of 5-(4-pyridinyl)-1H-indole-2,3-dione in 200 ml. of DMF and reaction of the resulting sodium salt with 10 g. (0.12 mole) of ethylene carbonate.

EXAMPLES 4A–4D

Following a procedure similar to that described in Example 2A above, the following compounds of formula I, where $R_1$ is methyl and Q is other than O, were prepared:

EXAMPLE 4A

1-Methyl-5-(4-pyridinyl)-1H-indole-2,3-dione 3-oxime hydrochloride, m.p. >315° C. (soft. 295° C.) (11.85 g., from methanol/diethyl ether), prepared by refluxing a mixture of 1-methyl-5-(4-pyridinyl)-1H-indole-2,3-dione with 17.37 g. (0.25 mole) of hydroxylamine hydrochloride in 300 ml. of pyridine.

EXAMPLE 4B

1-Methyl-5-(4-pyridinyl)-1H-indole-2,3-dione 3-hydrazone, m.p. 178°–180° C. (9.0 g., from aqueous DMF), prepared by refluxing a mixture of 31 g. (0.13 mole) of 1-methyl-5-(4-pyridinyl)-1H-indole-2,3-dione with 19 ml. (0.39 mole) of 85% hydrazine hydrate in 200 ml. of glacial acetic acid.

EXAMPLE 4C

1-Methyl-5-(4-pyridinyl)-1H-indole-2,3-dione 3-(2-hydroxyethyl)hydrazone, m.p. 210°–211° C. (6.75 g., from isopropanol), prepared by refluxing a mixture of 11.91 g. (0.05 mole) of 1-methyl-5-(4-pyridinyl)-1H-indole-2,3-dione with 10.2 ml. (0.15 mole) of (2-hydroxyethyl)hydrazine in 400 ml. of ethanol.

EXAMPLE 4D

1-Methyl-5-(4-pyridinyl)-1H-indole-2,3-dione 3-imidosemicarbazone, m.p. 304°–306° C. (12.1 g.), prepared by refluxing a mixture of 11.91 g. (0.05 mole) of 1-methyl-5-(4-pyridinyl)-1H-indole-2,3-dione, 7.49 g (0.06 mole) of aminoguanidine bicarbonate and 9.12 g. (0.07 mole) of sodium acetate trihydrate in a solution of 400 ml. of ethanol and 50 ml. of water.

EXAMPLE 4E

1-Methyl-5-(4-pyridinyl)-1H-indole-2,3-dione 3-methylhydrazone, m.p. 204°–205° C. (10.5 g., from methanol), prepared by refluxing a mixture of 11.91 g. (0.05 mole) of 1-methyl-5-(4-pyridinyl)-1H-indole-2,3-dione and 8.1 ml. (0.15 mole) of a 98% solution of N-methylhydrazine in 400 ml. of ethanol.

EXAMPLE 5

To a stirred, boiling suspension of 20.0 g. (0.09 mole) of 5-(4-pyridinyl)-1H-indole-2,3-dione in one liter of water was added, in portions over a six minute period, 26.4 g. (0.15 mole) of sodium hydrosulfite. The mixture was stirred at reflux for two hours, then chilled and filtered, and the resulting solid (18.8 g.) was recrystallized from methanol to give 7.8 g. of 2-oxo-5-(4-pyridinyl)-1H-indol-3-ol, m.p. 305°–350° C.

EXAMPLE 6

A stirred suspension of 27.3 g. (0.122 mole) of 5-(4-pyridinyl)-1H-indole-2,3-dione in 70 ml. of glacial acetic acid at 20° C. was treated dropwise with a solution of 38.0 g. (0.187 mole) of 3-chloroperbenzoic acid in 265 ml. of glacial acetic acid over a period of eighty-five minutes. When addition was complete, the temperature of the mixture was raised to 60° C., stirred for one hour and then allowed to cool to room temperature. The orange solid which had separated was collected by filtration, dried and recrystallized from 875 ml. of DMF to give 13.0 g. of 5-(4-pyridinyl)-1H-indole-2,3-dione-N-(Py)-oxide, m.p. 294°–295° C.

We claim:

1. A compound having the formula:

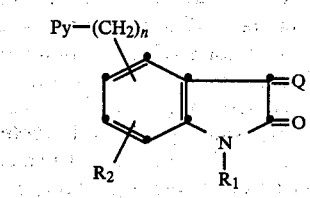

where Py represents the 4-pyridinyl group; $R_1$ represents hydrogen, lower-alkyl, hydroxy-lower-alkyl (having from two to seven carbon atoms, at least two of which are linear), di-lower-alkylamino-lower-alkyl or carbo-lower-alkoxy-lower-alkyl; $R_2$ represents hydrogen or lower-alkyl; Q represents O, H(OH), NOH, $NNH_2$, NNH(lower-alkyl), NN(lower-alkyl)$_2$, $NNHC_6H_5$, NNH(hydroxy-lower-alkyl) (having from two to seven carbon atoms, at least two of which are linear), NNCH(=S)NH$_2$, NNHC(=NH)NH$_2$ (only when $R_1$ is lower-alkyl), NNHCOCH$_2$N(lower-alkyl)$_3^+$ X$^-$ or NNHCOCH$_2$Pyr$^+$ X$^-$, where Pyr$^+$ is the pyridinium cation and X$^-$ in the latter two instances is the anion of sulfuric acid or a hydrohalic acid; n is 0 or the integer 1; the Py—(CH$_2$)$_n$ group occupies either the 4- or 5-position of the 1H-indole-2,3-dione nucleus; and the N—(Py)—oxides thereof; or a pharmaceutically acceptable acid-addition salt thereof, and where lower-alkyl, all occurrences other than specifically defined above, contains from one to seven carbon atoms.

2. A compound according to claim 1 where Q represents O, H(OH), NOH, $NNH_2$, NNH(lower-alkyl), NNH(hydroxy-lower-alkyl), NNHC(=S)NH$_2$, NNHC(=NH)NH$_2$ (only when $R_1$ is lower-alkyl), NNHCOCH$_2$N(lower-alkyl)$_3^+$ X$^-$ or NNHCOCH$_2$—Pyr$^+$ X$^-$; and $R_1$ represents hydrogen, lower-alkyl or hydroxy-lower-alkyl; or a pharmaceutically acceptable acid-addition salt thereof.

3. A compound according to claim 1 where Q represents O, H(OH), $NNH_2$, NNH(lower-alkyl), NN(lower-alkyl)$_2$, $NNHC_6H_5$, NNH(hydroxy-lower-alkyl) or NNHC(=S)NH$_2$; $R_1$ is hydrogen, lower-alkyl, di-lower-alkylamino-lower-alkyl or carbo-lower-alkoxy-lower-alkyl; the N-(Py)-oxides thereof; or an acid-addition salt thereof.

4. A compound according to claim 2 where $R_1$ is hydrogen; or an acid-addition salt thereof.

5. A compound according to claim 2 where $R_1$ is lower-alkyl; or an acid-addition salt thereof.

6. A compound according to claim 3 where $R_1$ is hydrogen; or an acid-addition salt thereof.

7. A compound according to claim 3 where $R_1$ is lower-alkyl; or an acid-addition salt thereof.

8. A compound according to claim 4 where the Py-(CH$_2$)$_n$ group is in the 5-position of the 1H-indole-2,3-dione nucleus; or an acid-addition salt thereof.

9. A compound according to claim 4 where the Py group is in the 4-position of the 1H-indole-2,3-dione nucleus; n is 0; or an acid-addition salt thereof.

10. A compound according to claim 5 where the Py group is in the 5-position of the 1H-indole-2,3-dione nucleus; n is 0; or an acid-addition salt thereof.

11. A compound according to claim 5 where the Py group is in the 4-position of the 1H-indole-2,3-dione nucleus; n is 0; or an acid-addition salt thereof.

12. A compound according to claim 6 where the Py-(CH$_2$)$_n$ group is in the 5-position of the 1H-indole-2,3-dione nucleus; or an acid-addition salt thereof.

13. A compound according to claim 6 where the Py group is in the 4-position of the 1H-indole-2,3-dione nucleus; n is 0; or an acid-addition salt thereof.

14. A compound according to claim 7 where the Py group is in the 5-position of the 1H-indole-2,3-dione nucleus; n is 0; or an acid-addition salt thereof.

15. 1-(2-Hydroxyethyl)-5-(4-pyridinyl)-1H-indole-2,3-dione according to claim 2.

16. Ethyl α-[5-(4-pyridinyl)-1H-indole-2,3-dion-1-yl]acetate methanesulfonate according to claim 3.

17. 1-[2-(Diethylamino)ethyl]-5-(4-pyridinyl)-1H-indole-2,3-dione trihydrochloride according to claim 3.

18. t-Butyl α-[5-(4-pyridinyl)-1H-indole-2,3-dion-1-yl]acetate according to claim 3.

19. 5-(4-Pyridinyl)-1H-indole-2,3-dione or the methanesulfonate salt thereof according to claim 8.

20. 2-Oxo-5-(4-pyridinyl)-1H-indol-3-ol according to claim 8.

21. 5-(4-Pyridinyl)-1H-indole-2,3-dione 3-(2-hydroxyethyl)hydrazone according to claim 8.

22. 5-(4-Pyridinyl)-1H-indole-2,3-dione 3-methylhydrazone according to claim 8.

23. 5-(4-Pyridinyl)-1H-indole-2,3-dione 3-(t-butyl)hydrazone according to claim 8.

24. 5-(4-Pyridinyl)-1H-indole-2,3-dione 3-thiosemicarbazone according to claim 8.

25. 5-(4-Pyridinyl)-1H-indole-2,3-dione 3-oxime hydrochloride according to claim 8.

26. 5-(4-Pyridinylmethyl)-1H-indole-2,3-dione 3-hydrazone according to claim 8.

27. 5-(4-Pyridinyl)-1H-indole-2,3-dione 3-[(trimethylammonium)acetyl]hydrazone chloride according to claim 8.

28. 4-Methyl-5-(4-pyridinyl)-1H-indole-2,3-dione according to claim 8.

29. 4-Methyl-5-(4-pyridinyl)-1H-indole-2,3-dione 3-[(trimethylammonium)acetyl]hydrazone chloride according to claim 8.

30. 5-(4-Pyridinyl)-1H-indole-2,3-dione 3-(pyridinium acetyl)hydrazone chloride according to claim 8.

31. 4-(4-Pyridinyl)-1H-indole-2,3-dione or the hydrochloride salt thereof according to claim 9.

32. 1-Methyl-5-(4-pyridinyl)-1H-indole-2,3-dione according to claim 10.

33. 1-Methyl-5-(4-pyridinyl)-1H-indole-2,3-dione 3-hydrazone according to claim 10.

34. 1-Methyl-5-(4-pyridinyl)-1H-indole-2,3-dione 3-(2-hydroxyethyl)hydrazone according to claim 10.

35. 1-Methyl-5-(4-pyridinyl)-1H-indole-2,3-dione 3-oxime hydrochloride according to claim 10.

36. 1-Methyl-5-(4-pyridinyl)-1H-indole-2,3-dione 3-imidosemicarbazone according to claim 10.

37. 1-Methyl-4-(4-pyridinyl)-1H-indole-2,3-dione according to claim 11.

38. 5-(4-Pyridinyl)-1H-indole-2,3-dione 3-(N,N-dimethyl)hydrazone according to claim 12.

39. 5-(4-Pyridinyl)-1H-indole-2,3-dione 3-hydrazone or the hydrochloride salt thereof according to claim 12.

40. 5-(4-Pyridinylmethyl)-1H-indole-2,3-dione according to claim 12.

41. 5-(4-Pyridinyl)-1H-indole-2,3-dione 3-phenylhydrazone according to claim 12.

42. 5-(4-(Pyridinyl)-1H-indole-2,3-dione-N-(Py)-oxide according to claim 12.

43. 6-Methyl-5-(4-pyridinyl)-1H-indole-2,3-dione according to claim 12.

44. 4-Methyl-5-(4-pyridinyl)-1H-indole-2,3-dione 3-hydrazone according to claim 12.

45. 4-(4-Pyridinyl)-1H-indole-2,3-dione 3-(N,N-dimethyl)hydrazone according to claim 13.

46. 4-(4-Pyridinyl)-1H-indole-2,3-dione 3-hydrazone according to claim 13.

47. 1-Methyl-5-(4-pyridinyl)-1H-indole-2,3-dione 3-methylhydrazone according to claim 14.

48. 5-(4-Pyridinyl)-1H-indole-2,3-dione 3-imidosemicarbazone.

* * * * *